US006651510B2

(12) United States Patent
Noma

(10) Patent No.: US 6,651,510 B2
(45) Date of Patent: Nov. 25, 2003

(54) METHOD AND APPARATUS FOR MONITORING ABNORMALITY OF MOLD-CLAMPING MECHANISM OF MOLDING MACHINE

(75) Inventor: Masanobu Noma, Ube (JP)

(73) Assignee: Ube Techno Eng. Co., Ltd., Yamaguchi (JP)

( * ) Notice: Subject to any disclaimer, the term of this patent is extended or adjusted under 35 U.S.C. 154(b) by 23 days.

(21) Appl. No.: 09/985,580

(22) Filed: Nov. 5, 2001

(65) Prior Publication Data

US 2003/0089179 A1 May 15, 2003

(51) Int. Cl.⁷ .............................................. G01N 3/02
(52) U.S. Cl. ............................................................ 73/856
(58) Field of Search ............................ 73/856; 425/169, 425/170, 149, 150; 264/40.1, 40.5, 40.7

(56) References Cited

U.S. PATENT DOCUMENTS

| 4,685,876 A | 8/1987 | Loscei ........................ 425/170 |
| 4,832,884 A | 5/1989 | Speck et al. ................ 264/40.5 |
| 4,869,659 A | * 9/1989 | Sakai et al. .................. 425/135 |
| 5,059,365 A | * 10/1991 | Hertzer et al. ............. 264/40.5 |
| 5,149,471 A | 9/1992 | Catanzaro et al. ......... 264/40.5 |
| 6,068,463 A | 5/2000 | Urbanek ...................... 425/169 |
| 6,157,158 A | 12/2000 | Ishikawa ..................... 318/626 |

FOREIGN PATENT DOCUMENTS

JP    2001-170752    * 6/2001

* cited by examiner

*Primary Examiner*—Max Noori
(74) *Attorney, Agent, or Firm*—Sughrue Mion, PLLC

(57) ABSTRACT

A method for monitoring abnormality of a mold-clamping mechanism of a molding machine and for estimating the amount of abrasion in the toggle mechanism without disassembling a mold-clamping mechanism in the molding machine to allow manual inspection. The timing and content of maintenance to be performed is determined based on measurements of stress at the toggle mechanism, from which the amount of abrasion in the toggle is calculated. This method makes it possible to operate the machine until the time just before a product quality deficiency occurs, thereby allowing maintenance to be performed with a minimum of machine disassembly for manual inspection.

23 Claims, 12 Drawing Sheets

30 : TOGGLE MECHANISM
44 : MOLD-CLAMPING MECHANISM ABNORMALITY MONITORING APPARATUS

A

B

A

B

OUTPUT

METHOD AND APPARATUS FOR MONITORING ABNORMALITY OF MOLD-CLAMPING MECHANISM OF MOLDING MACHINE

BACKGROUND OF THE INVENTION

1. Field of the Invention

The present invention relates to a method and an apparatus for monitoring abnormality of a mold-clamping mechanism of a molding machine, and particularly relates to a method and an apparatus for monitoring abnormality of a mold-clamping mechanism of a molding machine, capable of measuring the amount of aged deterioration of a mold-clamping mechanism used in a die casting machine, a resin injection molding machine or the like and judging the timing of inspection and maintenance of the mold-clamping mechanism.

2. Description of the Related Art

In molding machines typified by die casting machines and resin injection molding machines, many of them with use of toggle mechanisms for mold-clamping mechanisms are used for the purpose of obtaining large mold clamping force.

Such molding machines are operated for long years (5 to 10 years), and as a result, abrasion occurs to the rotational shaft bearing portions for connecting the links and the pins constituting the toggle mechanisms. When the abrasion increases, deviation occurs to the mold clamping force, whereby the problem that burrs generate at the mating surfaces of the metal mold or the toggle mechanism passes the change point (dead point) and the molds cannot be opened after the injection molding. Consequently, for the purpose of preventing these troubles, the mold-clamping mechanisms are disassembled periodically and direct measurement is performed to find out whether the abrasion amounts at the pins and shaft bearing portions exceed a threshold value.

However, the aforementioned conventional method requires tremendous workers' effort for disassembly inspection and re-assembly of the mold-clamping mechanism. Further, the expense for inspection and stop of the molding machine become necessary, which reduces productivity of the entire factory and causes great loss.

A method of attaching sensors to tie-bars constituting a mold-clamping mechanism and judging the deviation of the mold-clamping force with reference to the values from the sensors is known, but direct measurement of the toggle mechanism is not performed, and thus it is difficult to judge the degree of each abrasion at rotational bearing portions for connecting links and pins (constituting the toggle mechanism).

Disassembly inspection is effective only for secular change in abrasion, and an unexpected abnormality occurring during the operation of the molding machine (for example, increase in rotation load caused by poor lubrication at the rotating portions) cannot be monitored.

In view of the aforementioned conventional problems, an object of the present invention is to provide a method and an apparatus for monitoring abnormality of a mold-clamping mechanism of a molding machine, which estimate abrasion amount without disassembly inspection of the mold-clamping mechanism in the molding machine, make it possible to operate the machine until the time just before a quality deficiency of the product occurs, perform maintenance with the minimum disassembly inspection and improve productivity, and can detect an abnormal phenomenon even if an unexpected abnormality occurs to the mold-clamping mechanism.

SUMMARY OF THE INVENTION

A method and an apparatus for monitoring abnormality of a mold-clamping mechanism of a molding machine, which estimate an abrasion amount without disassembly for inspection of a mold-clamping mechanism in a molding machine and make it possible to operate the machine until the time just before a quality deficiency of a product occurs, perform maintenance with the minimum disassembly for inspection and improve productivity, are provided.

A die casting machine 10 uses a toggle mechanism 30 for a mold-clamping mechanism 16, and a strain gauge 40 is stuck to the toggle mechanism 30. The strain gauge 40 is connected to stress judging means 47 via a signal amplifier 42. The abrasion amount is calculated from the recorded data and the timing of maintenance of the mold-clamping mechanism is judged from the correlation between the abrasion amount and the quality of a molded product in the stress judging means 47, thereby making it possible to perform maintenance with the minimum disassembly inspection and improve productivity.

DETAILED DESCRIPTION OF THE PREFERRED EMBODIMENT

Figure 1:
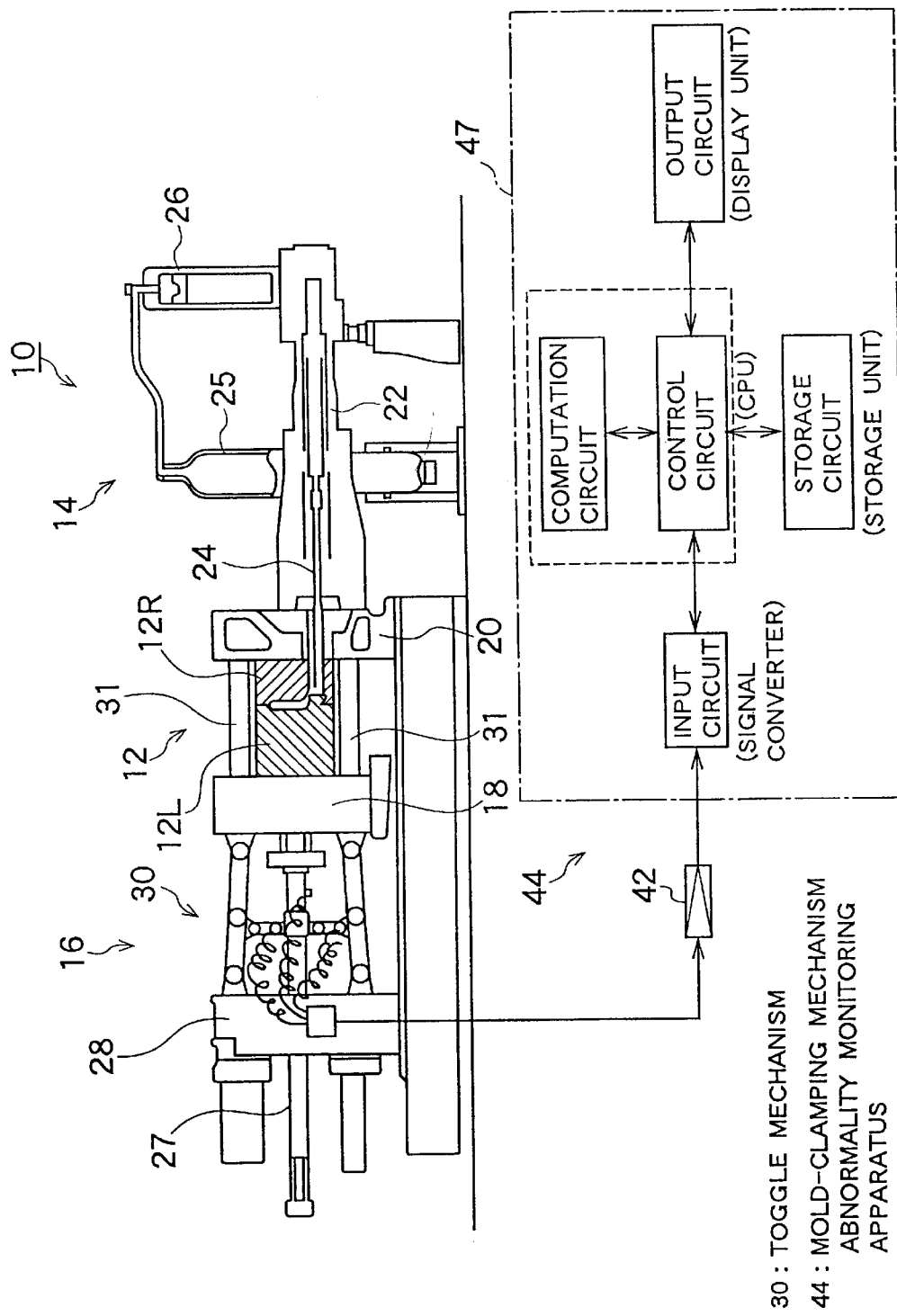
FIG. 1 is a side view showing a constitution of a die casting machine according to a present embodiment.

The present invention is made based on the knowledge that a degree of each abrasion at rotational shaft bearing portions for connecting links and pins constituting a toggle mechanism can be accurately estimated if stress exerted on the toggle mechanism is directly measured.

Specifically, a method for monitoring abnormality of a mold-clamping mechanism of a molding machine according to the present invention is a method for monitoring abnormality of a mold-clamping mechanism of a molding machine using a toggle mechanism for a mold-clamping mechanism, including the steps of measuring stress exerted on the aforementioned toggle mechanism, and comparing the measured value and a stress standard value set in advance to determine a content and timing of maintenance for the mold-clamping mechanism. Measuring the stress exerted on the toggle mechanism means to measure an amount of change in the stress exerted on each link member constituting the aforementioned toggle mechanism and the direction in which the stress is exerted (from compression to stretch, or vice versa) and to monitor abnormality occurring to the mold-clamping mechanism.

In concrete, a method for monitoring abnormality of a mold-clamping mechanism of a molding machine using, for a mold-clamping mechanism, a plurality of toggle mechanisms having mid-links, and cross-head links for extending the mid-links by pressing the mid-links, includes the steps of measuring stress exerted on a plurality of the aforementioned mid-links, and comparing the measured values and a stress standard value set in advance to estimate abrasion amounts of the aforementioned mid-links and difference in the abrasion amounts occurring to the mid-links and determine a content and timing of maintenance.

A method for monitoring abnormality of a mold-clamping mechanism of a molding machine using, for a mold-clamping mechanism, a plurality of toggle mechanisms having mid-links, and cross-head links for extending the mid-links by pressing the mid-links, includes the steps of measuring stress occurring to the aforementioned cross-head links after mold-clamping, and comparing the measured values and a stress standard value set in advance to estimate absolute magnitudes of the abrasion amounts of the aforementioned mid-links and determine a content and timing of maintenance.

Alternatively, a method for monitoring abnormality of a mold-clamping mechanism of a molding machine using, for a mold-clamping mechanism, a plurality of toggle mechanisms having mid-links, and cross-head links for extending the mid-links by pressing the mid-links, includes the steps of measuring stress exerted on a plurality of the aforementioned mid-links and stress occurring to the aforementioned cross-head links after mold-clamping, and comparing the measured values and a stress standard value set in advance to estimate difference in the abrasion amounts occurring to the mid-links and absolute magnitudes of the abrasion amounts of the aforementioned mid-links and determine a content and timing of maintenance.

Here, the difference in the abrasion amounts occurring to the aforementioned mid-links may be obtained by using a deviation from the maximum value of the measured values measured at a plurality of the aforementioned mid-links, or may be obtained by using a deviation from the measured value of the aforementioned mid-link, which increases first of those of a plurality of the aforementioned mid-links. The aforementioned toggle mechanism may comprise a set of upper and lower cross-head links and it may be suitable to judge a state of the mid-links at the time of completion of mold-closing from a stress pattern during one cycle of mold-clamping.

The aforementioned stress standard value is set to be larger than a stress value calculated from injection pressure of the aforementioned molding machine.

An apparatus for monitoring abnormality of a mold-clamping mechanism of a molding machine according to the present invention is a molding machine using a toggle mechanism for a mold-clamping mechanism, comprises stress measuring means provided at the aforementioned toggle mechanism, and stress judging means having a stress standard database set in advance, to which the aforementioned stress measuring means is connected, and a measured value from the aforementioned stress measuring means is taken into the aforementioned stress judging means and checked against the aforementioned stress standard database and thereby a content and timing of maintenance are outputted.

Here, the aforementioned toggle mechanism comprises a plurality of mid-links and cross-head links for extending the mid-links by pressing the mid-links, and the aforementioned stress measuring means are provided at the mid-links to make it possible to measure abrasion amounts of the aforementioned mid-links and difference in the abrasion amounts occurring to the mid-links.

The aforementioned toggle mechanism comprises a plurality of mid-links and cross-head links for extending the mid-links by pressing the mid-links, and the aforementioned stress measuring means are preferably provided at the cross-head links to make it possible to measure absolute magnitudes of abrasion amounts of the aforementioned mid-links.

Alternatively, the aforementioned toggle mechanism comprises a plurality of mid-links and cross-head links for extending the mid-links by pressing the mid-links, and the aforementioned stress measuring means are preferably provided at the mid-links and the cross-head links to make it possible to measure difference in abrasion amounts occurring to the aforementioned mid-links and absolute magnitudes of the abrasion amounts of the aforementioned mid-links, and a strain gauge is used for the aforementioned stress measuring means and stress is preferably calculated based on a value of the strain gauge.

Stress calculation may be performed by using ultrasound as the stress measuring means instead of the strain gauge, and in this case, non-contact measurement is made possible, which can omit an operation of attaching it to the toggle mechanism and the like. With use of the strain gauge and ultrasound in combination, measurement accuracy can be improved, and even if an abnormality occurs to one of them, the measurement can be continued at the other one, thus making it possible to improve reliability of the stress measuring means.

As for the factors that reduce availability of a molding machine, reduction in yields of the products and a poor operation of the machine itself are cited. If the quality is monitored with respect to the correlation between stress on the mid-links in the toggle mechanism section and the quality of the molded products, and if the poor operation of the machine is monitored mainly with respect to the correlation between stress on the cross-head links and operability of the machine, it becomes possible to judge the timing of maintenance for the mold-clamping mechanism from the estimated abrasion amount, thus making it possible to reduce the number of times for stopping the operation of the molding machine. Hence, availability of the molding machine can be improved while the quality of the molded products manufactured by the molding machine can be improved.

Specifically, according to the aforementioned structure, stress exerted on the toggle mechanism is measured, and the measured value is checked against the stress standard value that is found by the measurement in advance, whereby the abrasion amount in the toggle mechanism can be estimated. Consequently, it is not necessary to disassemble the toggle mechanism at each time when the abrasion amount of the toggle mechanism needs to be found, thus making it possible to improve availability of the molding machine as well as to maintain the quality of the molded products manufactured by the molding machine. Further, monitoring the stress exerted on the toggle mechanism all the time makes it possible to cope with an unexpected abnormal phenomenon. Specifically, if poor sliding or the like occurs to the toggle mechanism, the change appears as a change in the stress value occurring to the toggle mechanism, and therefore, if the measured value is checked against the stress standard value to obtain the content and timing of maintenance, it becomes possible to cope with an unexpected abnormal phenomenon occurring to the toggle mechanism.

The toggle mechanism comprises a plurality of the mid-links and cross-head links, and if the stresses exerted on the mid-links are measured, and the measured values are checked against the stress standard value, the abrasion amounts in the mid-links can be estimated. The difference in the variations in the stresses occurring to a plurality of the mid-links is taken, and thus the difference in the abrasion amount from one another, that is, the deviation abrasion amount can be found. An unexpected abnormal phenomenon occurring to the mid-links appears as a change in the stress values of the mid-links, and therefore, if the measured values are checked against the stress standard value to obtain the content and timing of maintenance, it goes without saying that an unexpected abnormal phenomenon occurring to the mid-links can be handled.

Further, the stresses exerted on the cross-head links after mold-clamping are measured, and the measured values are checked against the stress standard value, whereby the absolute magnitude of the abrasion amount in the mid-links can be estimated. Specifically, in the cross-head link, when the abrasion of the mid-link is small, the mid-link is not allowed to pass the change point, and the compressing stress is exerted on the aforementioned cross-head link at the time of the mold-clamping. However, when the abrasion of the mid-link develops, the mid-link hangs loose due to gravity, and the position of the mid-link at the time of the mold-clamping comes closer to the change point to reduce the aforementioned compressing stress, or it passes the aforementioned change point to make the toggle with the reverse mid-link, whereby stretching stress is exerted on the aforementioned cross-head. Subsequently the measured value of the cross-head link is checked against the relationship between the stress standard value of the cross-head link and the abrasion amount of the mid-link, whereby the absolute magnitude of the abrasion amount of the mid-link can be obtained. If the mid-link unexpectedly passes the change point due to the factors of an outer force and the like, the direction (stretching or compressing) of the stress exerted on the cross-head link during the mold-clamping changes, and if the stress on the aforementioned cross-head link is always monitored, a trouble of the mid-link passing the change point can be detected.

The stress exerted on a plurality of the aforementioned mid-links and the stress occurring to the aforementioned cross-head links after the mold-clamping are measured at the same time, and the measured values are checked against the stress standard value set in advance, whereby the difference in the abrasion amounts occurring to the mid-links and the absolute magnitudes of the abrasion amounts of the aforementioned mid-links can be estimated as described above.

Here, when the difference in the abrasion amounts occurring to the mid-links is obtained with use of the deviation from the maximum value of the aforementioned measured values measured at a plurality of the aforementioned mid-links, it can be judged that the mid-link with the largest measurement value out of a plurality of the mid-links has the smallest abrasion amount, and therefore, with the mid-link having the smallest abrasion amount being used as the reference, more accurate deviation abrasion amount can be obtained. Since there is the correlation between the measurement value and the difference in time at which the stress is exerted in a plurality of the mid-links, the difference in the abrasion amounts occurring to the mid-links may be obtained with reference to the measurement value of the mid-link, which rises first of a plurality of the mid-links.

Further, the stress standard value is set to be larger than the stress value calculated from the injection pressure of the molding machine, and thereby, even if the molten metal is injected into the metal mold after the mold-clamping, the metal-mold is never pressed to open by the injection pressure. Consequently, a burr can be prevented from occurring to mating surfaces (parting line) of the metal mold.

In the mold-clamping mechanism in the molding machine, the toggle mechanism is provided with the stress measuring means, thereby making it possible to measure the stress exerted on the toggle mechanism during the mold-clamping of the molding machine. The measured value is connected to the stress judging means, which previously stores the relationship between the abrasion amount and the stress value, that is, the stress standard database, thus making it possible to estimate the abrasion amount from the value of the aforementioned measured value. It can be judged whether the value of the abrasion amount influences the quality of the molded product and the operability of the machine or not, whereby it is not necessary to disassemble the toggle mechanism for check, and the availability of the molding machine can be improved. With use of a strain gauge (distortion gauge) for the measuring means, the strain occurring to the toggle mechanism can be measured, and the stress can be easily obtained by computing the measured strain with use of the numeral values of the respective components constituting the toggle mechanism.

A preferred embodiment of a method for monitoring abnormality of a mold-clamping mechanism of a molding machine and a molding machine according to the present invention will be explained in detail below with reference to the drawings.

FIG. 1 is a side view showing a constitution of a die casting machine according to the present embodiment. A die casting machine 10 being a molding machine as shown in FIG. 1 is constituted by three parts according to the purposes. More specifically, a metal mold 12 divided into a stationary side and a moving side, an injection mechanism 14 for feeding molten aluminum to an inside (metal mold cavity) of the metal mold 12, and a mold-clamping mechanism 16 connected to a moving side metal mold 12L (a stationary side metal mold is 12R) in the aforementioned metal mold 12, for moving the moving side metal mold 12L back and forth to thereby open and close the metal mold 12.

The metal mold 12 is constituted by the moving side metal mold 12L and the stationary side metal mold 12R as described above, and a shape of a molded product to be produced is formed inside the metal mold 12 (In the metal mold 12, shapes of a plurality of molded products are formed in the metal mold 12 and a plurality of molded products are produced at the same time in one injection process in some cases). The moving side metal mold 12L is attached to a moving platen 18 and connected to the mold-clamping mechanism 16 via the moving platen 18, while the stationary side metal mold 12R is attached to a stationary platen 20 to be fixed to the molding machine body.

The injection mechanism 14 for injecting molten aluminum (hereinafter, called molten metal) into the metal mold 12 is constituted by an injection cylinder 22, a piston 26, and an accumulator 25.

It goes without saying that the timing of injection of molten metal is linked to the timing of opening and closing the metal mold 12 by the mold-clamping mechanism 16.

The mold-clamping mechanism 16 for performing an operation of opening and closing the metal mold 12 is constituted by the moving platen 18 for fixing the moving side metal mold 12A thereto, a link housing 28 placed to sandwich the moving platen 18 with a stationary platen 20 and having a hydraulic mold-clamping cylinder 27, a toggle mechanism 30 provided between the aforementioned moving platen 18 and the aforementioned link housing 28, and a tie-bar 31 for connecting the stationary platen 20 and the housing 28.

The tie-bar 31 is inserted through each corner portion of the stationary platen 20 and the link housing 28 in this embodiment (four tie-bars in this embodiment), and the mold-clamping cylinder 27 is fitted into a center portion surrounded by the tie-bars 31 in the link housing 28.

The toggle mechanism 30 is provided between a guide rod 32 being a rod in the mold-clamping cylinder 27 and the moving platen 18 to connect both of them. This die casting machine 10 is loaded with a mechanism for automatically moving the position of the link housing 28 forward to secure clamping force when abrasion occurs to mid-links (the mid-links will be described later) constituting the toggle mechanism 30 and the clamping force reduces (when it reduces by about 5%).

FIG. 2(A) and FIG. 2(B) are explanatory views showing a constitution of the toggle mechanism 30. As shown in FIG. 2(A) and FIG. 2(B), a set of the toggle mechanisms 30 are provided each at an upper and lower side with respect to the aforementioned guide rod 32. The toggle mechanism 30 is constituted by cross-head links 34 connected to a tip end of the guide rod 32 with pins, toggle links 36 connected to the cross-head links 34 with pins with the other ends being connected to the link housing 28 with pins, and mid-links 38 connected to the cross-head links 34 with pins, similarly to the toggle links 36, with the other ends being connected to the moving platen 18. The toggle mechanism 30 is constituted by the cross-head links 34, the toggle links 36, and the mid-links 38 as described above, and the dimension of the toggle links 36 and the mid-links 38 when they are fully extended is set to be larger than the length of the tie-bar 31, whereby an increasing rate of a closing force is small while a closing speed is high at the first stage of the mold closing step of the metal mold 12 and the increasing rate of the closing force can be increased as the mold closing step nears to the end (while the mold closing speed of the moving platen 18 reduces following the increase in the increasing rate of the force) by only moving the cross-head links 34. Thus, by only moving the guide rod 32 back and forth, strong mold clamping force can be obtained in both of mold clamping and opening operations. Since pressure inside a metal mold cavity is generally set at $50 \sim 70 * 10^6 N/m^2$, the mold clamping force is set at a value not exceeding a force applied to the metal mold by the injection pressure (The mold clamping force is $1 \sim 40 * 10^6 N$).

Figure 3:
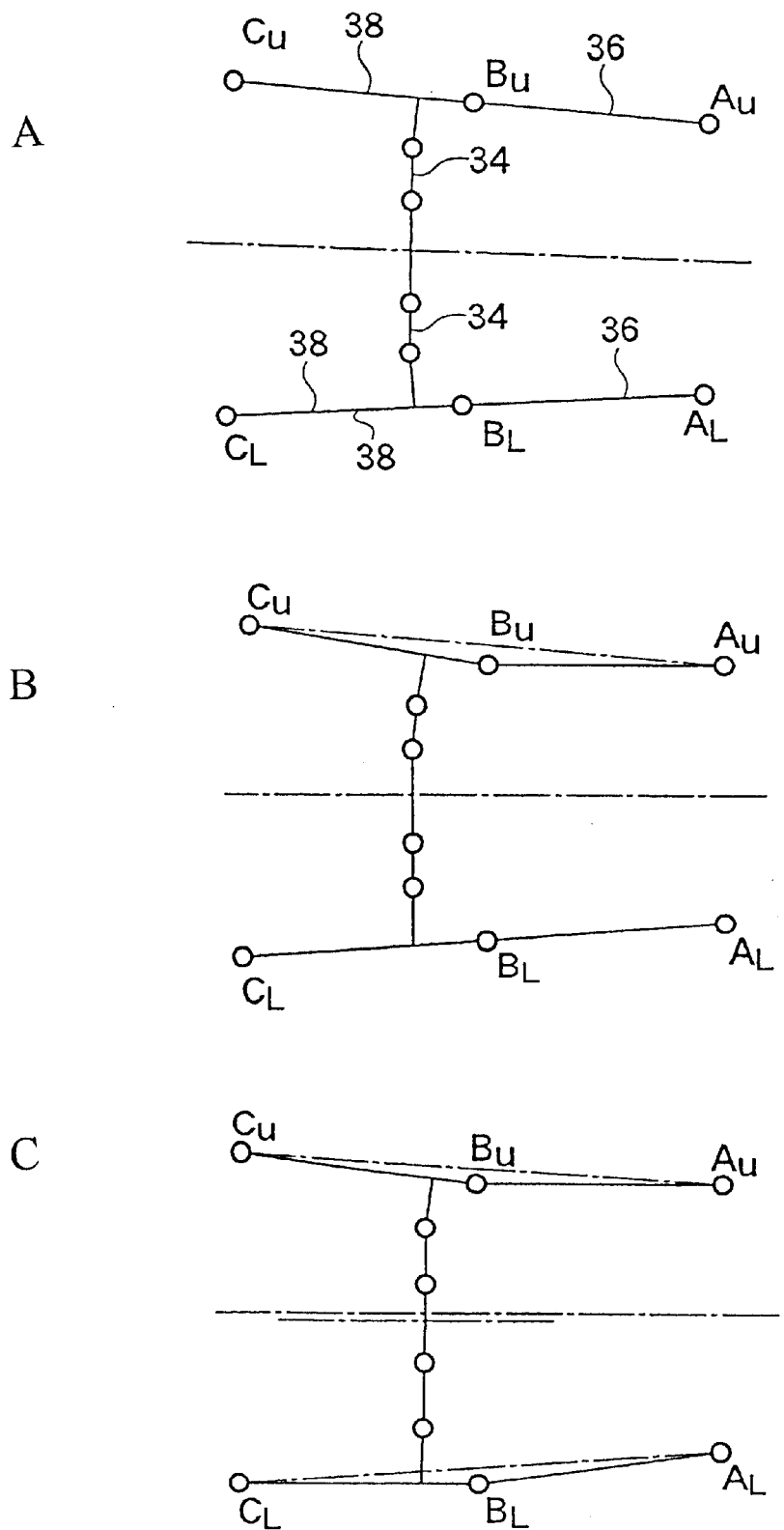
FIG. 3(A), FIG. 3(B) and FIG. 3(C) are explanatory phase diagrams showing operational conditions of the toggle mechanism.

FIG. 3(A), FIG. 3(B), and FIG. 3(C) are explanatory phase views showing operation conditions of the toggle mechanism. As the condition under which the toggle mechanism 30 operates normally, the state shown in FIG. 3(A) is necessary. More specifically, it is necessary that pin center points Au, Bu and Cu of the toggle link 36 and the mid-link 38 are on a straight line at a point of time when mold clamping is completed. However, with respect to the aforementioned state, in states as shown in both FIG. 3(B) and FIG. 3(C), a quality deficiency and poor operation are caused, whereby the normal continuous operations cannot be performed.

In concrete, in the case of FIG. 3(B), the force is insufficient at the upper side, whereby the mold opens during the injection of molten metal, and the aforementioned molten metal spouts out of it, which causes a burr and the fear that a quality deficiency of the molded product occurs. In the case of FIG. 3(C), since the point BL in FIG. 3(C) exceeds the change point, it becomes impossible to open the mold after the injection of the molten metal, whereby the cycle is stopped. Further, also in FIG. 3(C) as in FIG. 3(B), the mold opens during the molten metal injection and the aforementioned molten metal spouts out of it, thus causing a burr and the fear that the quality deficiency of the molded product occurs.

Figure 2:
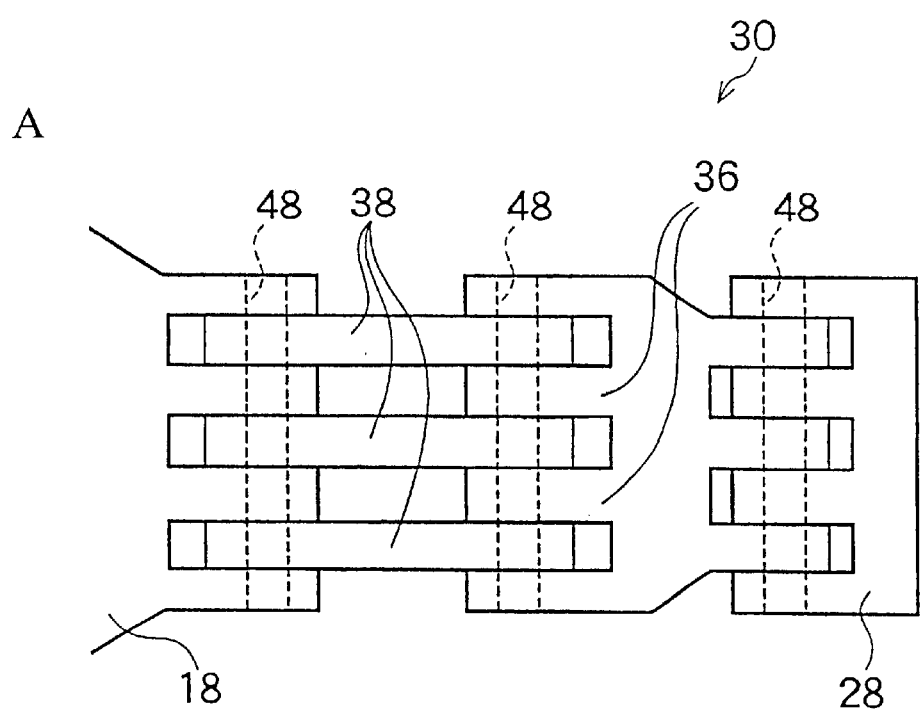
FIG. 2(A) and FIG. 2(B) are explanatory views showing a constitution of a toggle mechanism 30.
Figure 2:
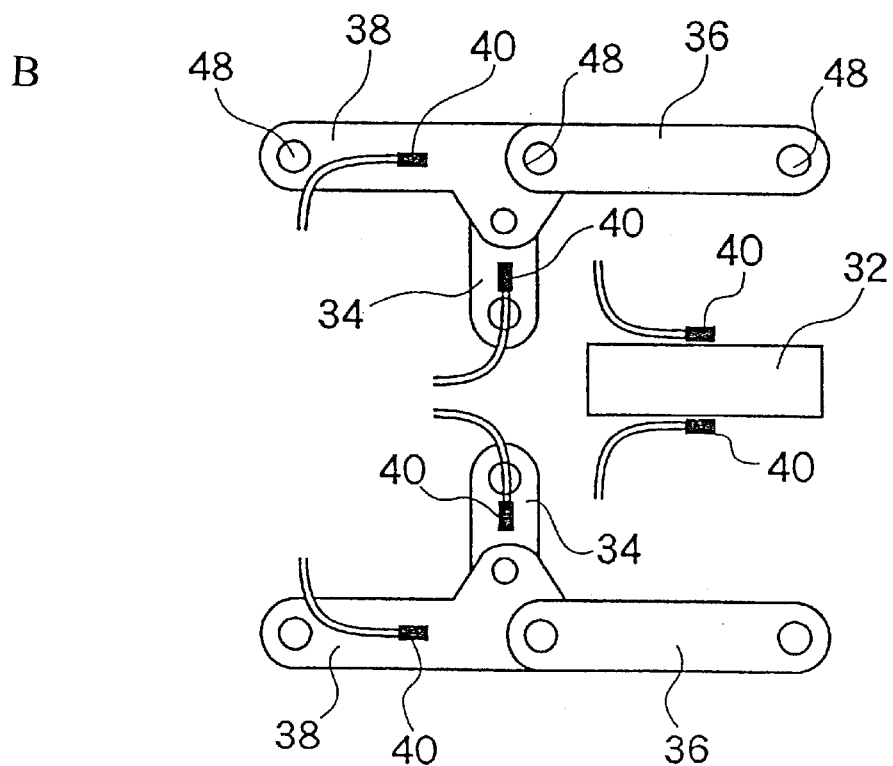

As shown in FIG. 2, a plurality of the cross-head links 34, the toggle links 36 and the mid-links 38 are normally provided, and in this embodiment, the toggle mechanism 30 is constituted by the two cross-head links 34, the two toggle links 36, and the three mid-links 38 as shown in FIG. 2(A), and they are connected to each other in a shape of teeth of a comb.

In the die casting machine 10 constituted as above, strain gauges 40 are stuck to the toggle mechanism 30 and the tie-bars 31.

In the toggle mechanism 30, the strain gauges 40 are stuck to all the three mid-links 38, and are also stuck to all the two cross-head links 34 and toggle links 36, so that the strain in a horizontal direction of each of the links can be measured.

In the guide rod 32, the strain gauges 40 are also stuck to the upper and lower sides thereof at which the link mechanisms 31 are provided, so 30 that the amount of strain added to the upper and lower link mechanisms 31 can be measured.

Figure 4:
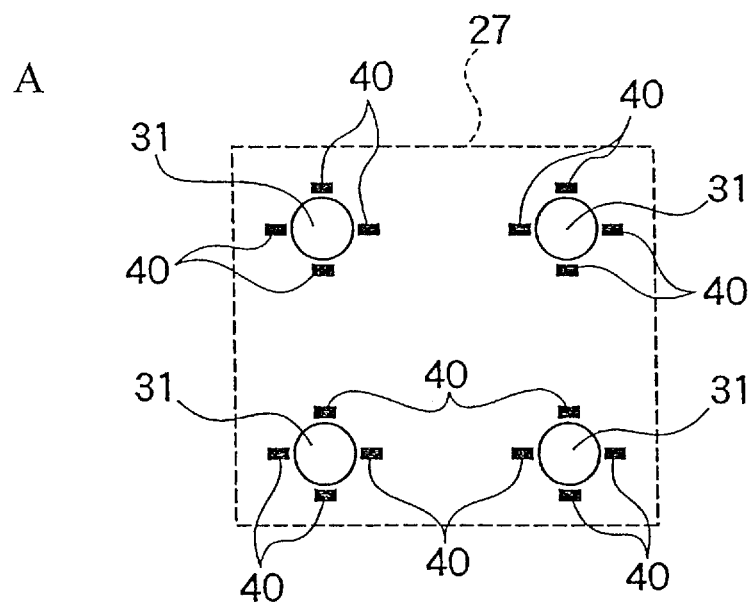
FIG. 4(A) and FIG. 4(B) are explanatory diagrams showing sticking positions for strain gauges in tie-bars 31.
Figure 4:
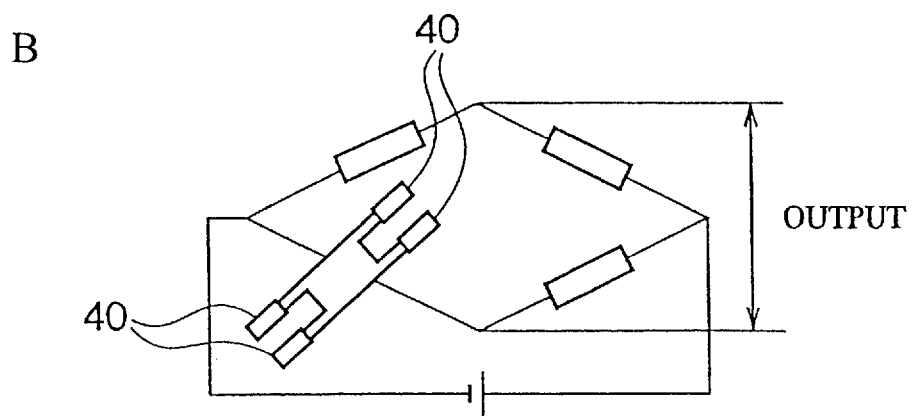

FIG. 4 is an explanatory view showing the sticking positions of the strain gauges in the tie-bars 31. As shown in FIG. 4(A), the tie-bars 31 are each inserted through each of the corner portions of the stationary platen 20 and the link housing 28, and their sectional forms are circular. About four of the strain gauges 40 are stuck to the circumferential surface of the tie-bar 31 to be along it (equally spaced at 90 degrees).

The strain gauges 40 stuck to the circumferential surface of the tie-bars 31 are connected in a bridge form as shown in FIG. 4(B) so as to obtain the average value of the four strain gauges 40.

The strain gauges 40 stuck to the toggle mechanism 30 and the tie-bars 31 as described above are connected to a signal amplifier 42 as shown in FIG. 1, and the output from the strain gauges 40 is amplified by the aforementioned signal amplifier 42. The data amplified by the signal amplifier 42 is inputted into stress judging means 47 connected to a rear stage of the aforementioned signal amplifier 42, and the maintenance content for the toggle mechanism 30 and the timing thereof are judged in the stress judging means 47. The strain gauges 40, the signal amplifier 42, and the stress judging means 47 are called a mold-clamping mechanism abnormality monitoring apparatus 44 as a single unit.

Figure 9:
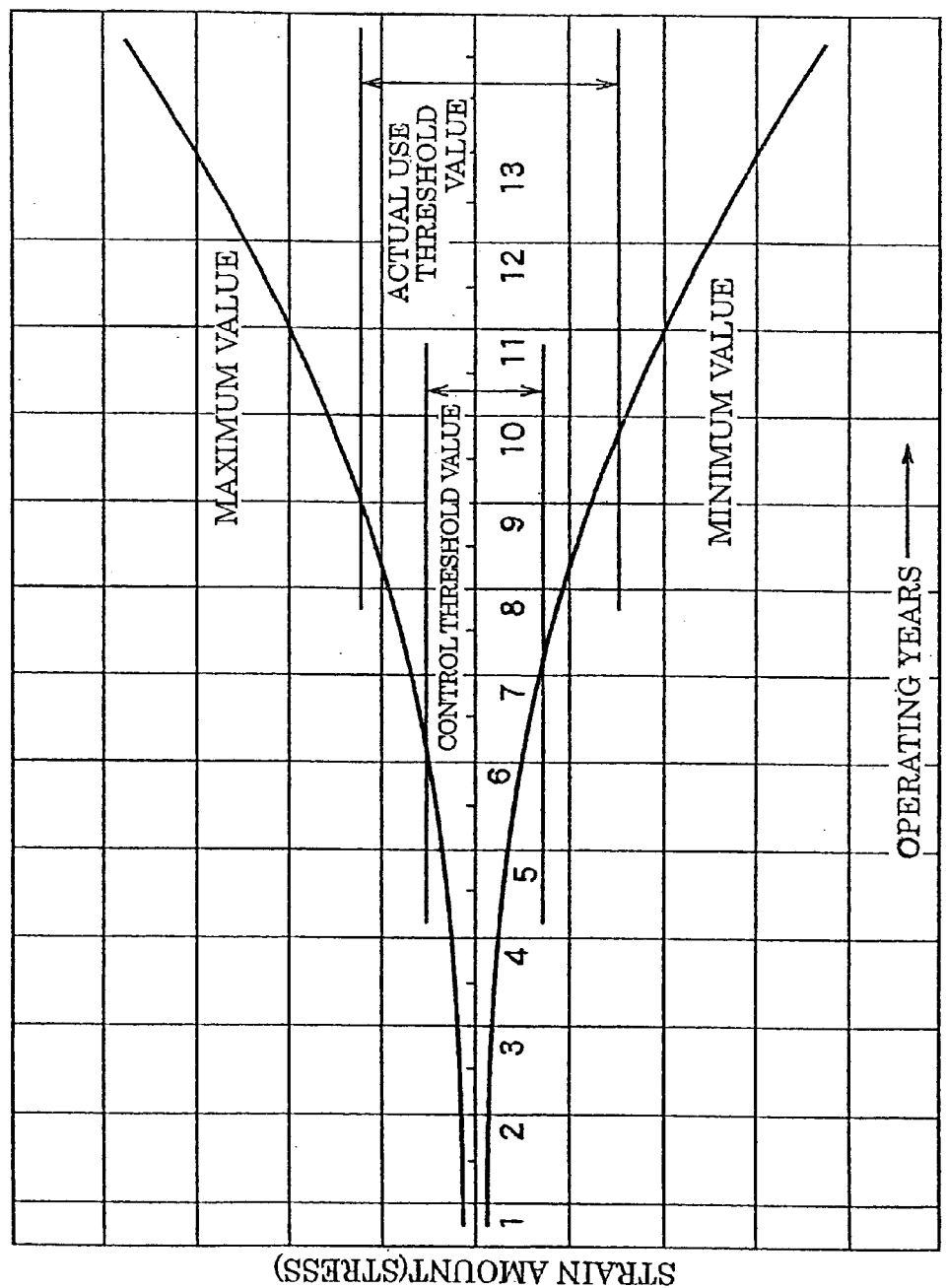
FIG. 9 is a graph showing an amount of strain (or stress) with respect to operating years in the mid-link 38.

Specifically, the stress judging means 47 incorporates stress standard database showing relationship of the amount of abrasion with respect to a stress value calculated in consideration of a calculated value in design and an actual measured value obtained from actual measurement of the actual thing, and data is checked against a stress standard value of the stress standard database, whereby the amount of abrasion can be calculated. The construction method of the stress standard database will be described later (See FIG. 10 and FIG. 11), and in this embodiment, the stress standard value showing the amount of strain (or stress) with respect to the number of operating years in the mid-link 38 is shown in FIG. 9.

A method of measuring an amount of abrasion occurring to the die casting machine 10 will be explained with use of the die casting machine 10 constituted as above.

The signal amplifier 42 and the stress judging means 47 are powered on, so that the data from the strain gauges 40 stuck to the toggle mechanism 30 and the tie-bars 31 can be inputted into them. Next, the arbitrary strain gauge 40 is selected, and the strain occurring to the die casting machine 10 during operation is actually measured. Selecting the arbitrary strain gauge 40 in this situation makes it possible to collect various kinds of data.

Figure 5:
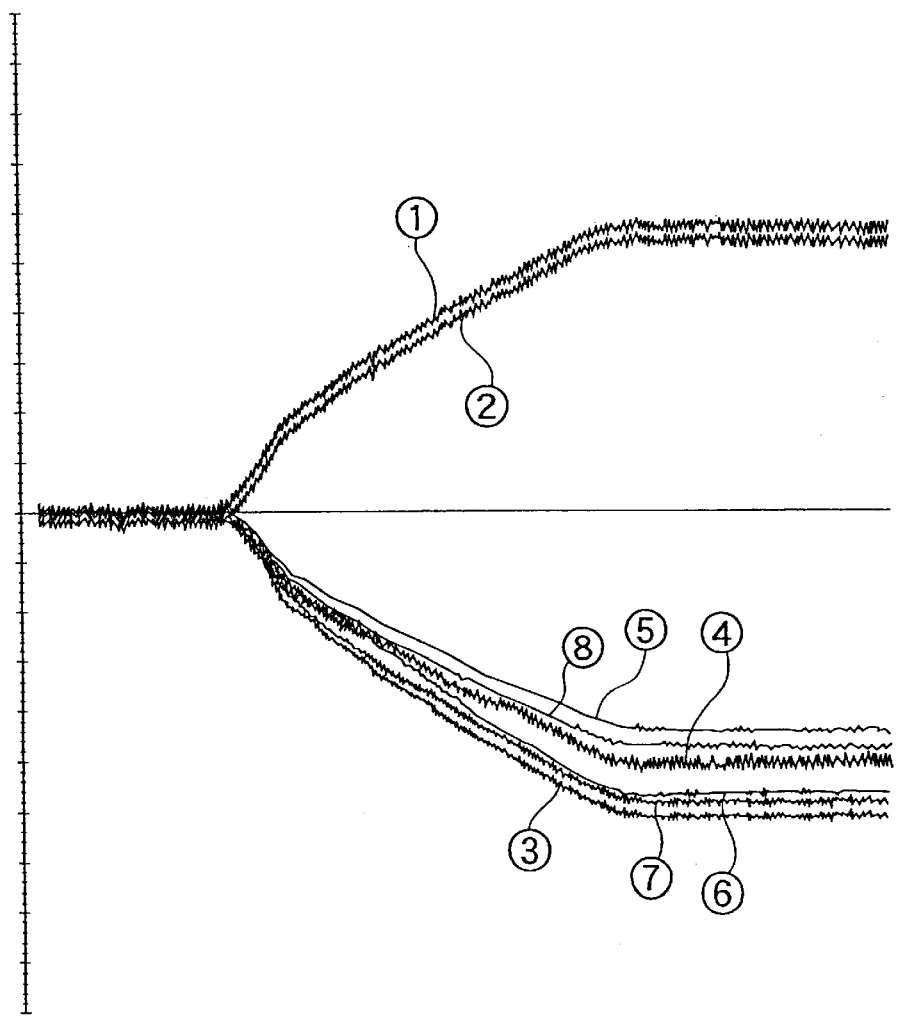
FIG. 5 is a graph showing transition of stresses occurring to the tie-bars 31 and mid-links 38 in an initial state.
Figure 6:
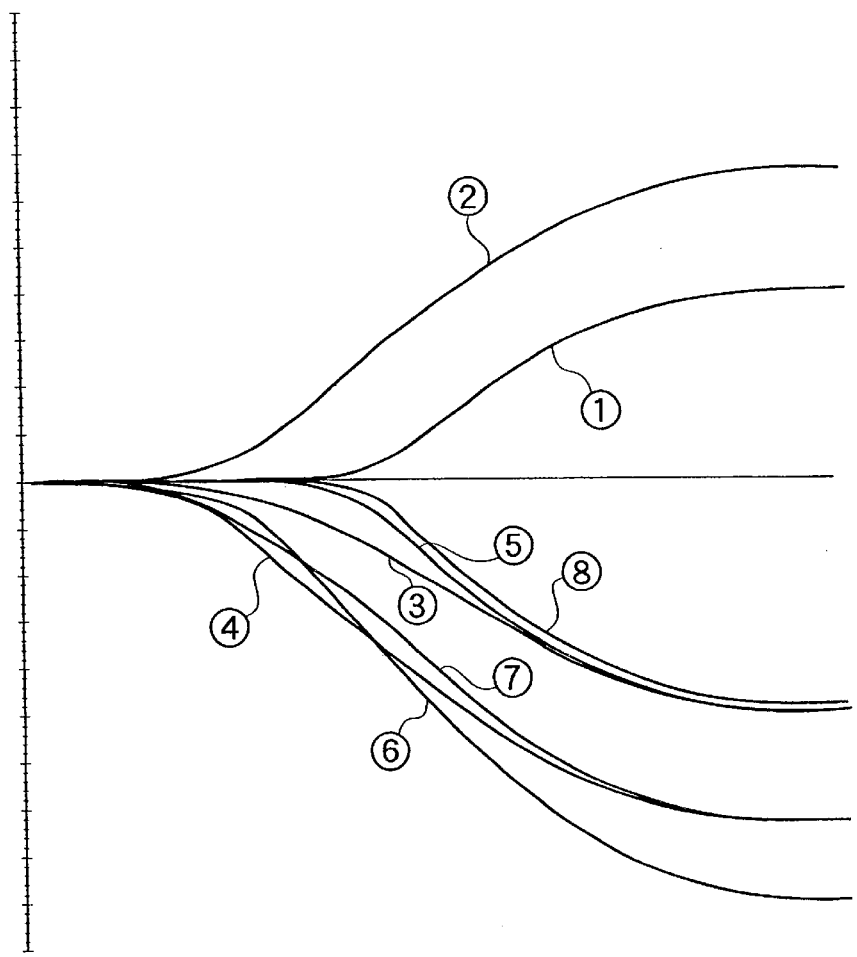
FIG. 6 is a graph showing transition of stresses occurring to the tie-bars 31 and the mid-links 38 in a state in which abrasion develops.

FIG. 5 is a graph showing the transition of the stresses occurring to the tie-bars 31 and the mid-links 38 in the early state. FIG. 6 is a graph showing the transition of the stresses occurring to the tie-bars 31 and the mid-links 38 in the state in which abrasion has developed.

In each of the graphs shown in FIG. 5 and FIG. 6, the vertical axis represents a stress value (a stretching direction is positive, and a compressing direction is negative), and the horizontal axis represents a time axis to show the transition of the stress values with the lapse of time from the state in which the mold is open to the completion of mold clamping. The numerals ① through ⑧ plotted in the graphs represent the measurement spots in the table below.

TABLE 1

| Channel No | Positions for sticking strain gauges |
|---|---|
| ① | Upper tie-bar operation side |
| ② | Upper tie-bar non-operation side |
| ③ | Upper mid-link operation side |
| ④ | Upper mid-link center |
| ⑤ | Upper mid-link non-operation side |
| ⑥ | Lower mid-link operation side |
| ⑦ | Lower mid-link center |
| ⑧ | Lower mid-link non-operation side |

When the tie-bars 31 and the mid-links 38 are in an initial state, that is, in the state in which abrasion does not develop, the difference in the stress value occurring to the tie-bars 31 and the mid-links 38 is small, and the clamping force is substantially uniform. However, abrasion occurs to the mid-links 38, and when it is developing, the difference in the stress value occurring to the tie-bars 31 and the mid-links 38 becomes large as shown in FIG. 6, whereby deviation occurs to the clamping force.

As for the difference in the stress value of the mid-links 38, the deviation is taken with reference to the largest value in each of the upper and lower toggle mechanisms 30. Specifically, the mid-link 38 having the largest stress value has a smaller amount of abrasion than the other mid-links 38 and thus receives larger stress than the other mid-links 38. Therefore, if the stress value of this mid-link 38 is taken as the reference, the difference in the stress value form the other mid-links 38, and the difference in the amount of abrasion as well can be correctly obtained. As series of this operation is performed by checking the stress value against the stress standard value in the stress standard database in the stress judging means 47, then calculating the amount of abrasion with respect to the stress value, and thereafter taking the difference in the amount of abrasion to set it as a deviation of the abrasion amount. The deviation abrasion amount is measured with reference to the mid-link 38 having the largest stress value, and if the value exceeds the standard stress value set in advance, the maintenance of the mid-link 38 is performed, or, even if the value does not exceed the standard stress value, the timing of maintenance can be judged from the deviation abrasion amount. In the present embodiment, the reference mid-link 38 is set based on the largest stress value, but this is not restrictive, and the deviation abrasion amount may be calculated, for example, with reference to the time at which stress is applied to the mid-link 38 first in the process from the metal mold opening to the mold clamping. This is because the mid-link 38 having the largest stress value has a smaller abrasion amount at a pin connecting portion 48 and the deviation abrasion amount can be also correctly measured with reference to the point of time at which stress is applied first.

If the difference in the stress measured at the upper and lower mid-links 38 is checked, the difference in the abrasion amount between the upper and lower links can be calculated, and since the strain gauges 40 are also stuck to the four tie-bars 31, the deviation of the force in the tie-bars 31 can be detected. The calculated value from the tie-bars 31 is checked against the calculated value in the mid-links 38, whereby the deviation of the mold clamping force in the die casting machine 10 can be estimated with high precision.

As described above, when abrasion occurs to the pin connecting portion 48 in the mid-link 38 and the mold clamping force reduces by about 5%, the link housing 28 automatically moves forward to compensate the mold clamping force reduced by the abrasion. However, when abrasion occurs to the pin connecting portions 48 in the upper and lower toggle mechanism 30, and if the toggle mechanisms 30 are in a state without load (in a so-called mold opening state), each link moves downward by the tare weight (hangs loose) so as to fill up a space at the pin connecting portion 48. In the upper toggle mechanism 30, the tare weight exerts in a direction to close the mid-link 38 and the toggle link 36, and while in the lower toggle mechanism 30, the tare weight exerts in a direction to open the mid-link 38 and the toggle link 36.

Figure 7:
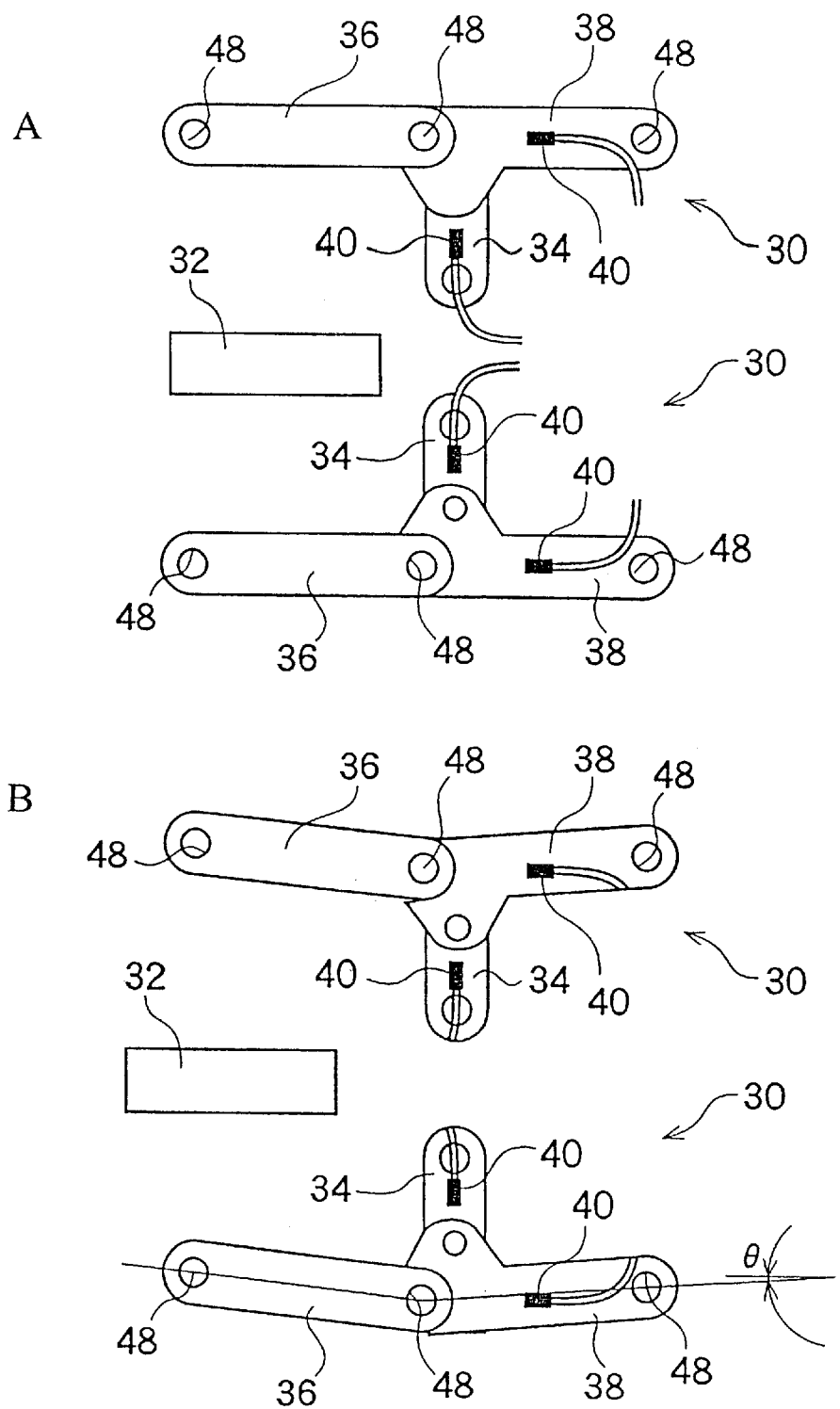
FIG. 7(A) and FIG. 7(B) are explanatory phase diagrams showing a case in which the toggle mechanism operates normally and in a case in which the toggle mechanism passes a change point.
Figure 8:
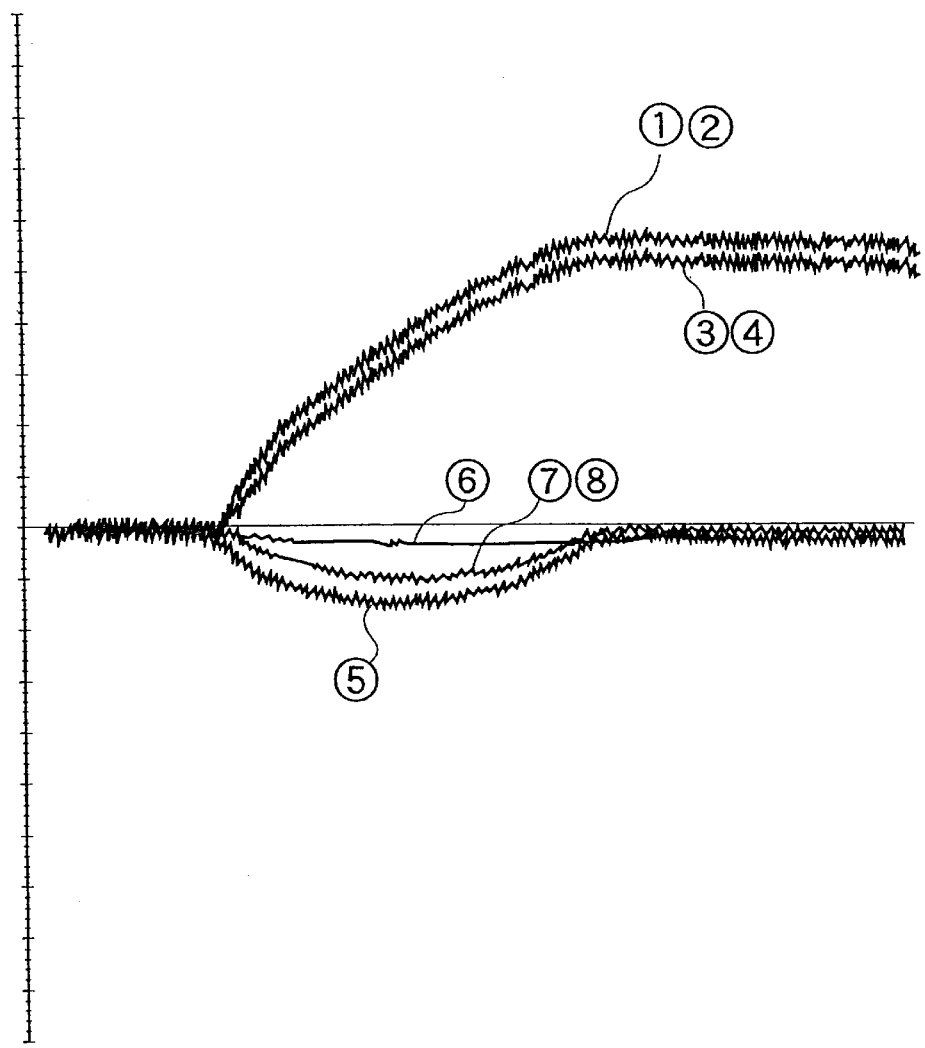
FIG. 8 is a graph showing transition of stresses occurring to the toggle mechanism.

If the degrees of opening of the upper and lower toggle mechanisms 30 differ due to abrasion occurring to the toggle mechanisms 30, and when the mold clamping cylinder 27 is operated to shift from the mold opening state to the mold clamping state, the relative positions of the mid-links 38 and the toggle links 36 differ as the initial state in the upper and lower toggle mechanisms 31, and therefore the starting times for clamping differ (specifically, since the lower toggle mechanism 30 is in a state of being opened to a large extent by the tare weight, the starting time for clamping is earlier in the lower toggle mechanism 30 as compared with the upper toggle mechanism 30). As a result, when sufficient clamping force is to be obtained by extending the mid-links 38 and the toggle links 36 constituting the upper toggle mechanism 30, there arise a possibility that the mid-links 38 and the toggle links 36 passes the change point (a so-called reverse toggle state). FIG. 7(A) and FIG. 7(B) are phase explanatory views showing a case in which the toggle mechanisms operate normally and a case in which the toggle mechanism passes the change point. FIG. 8 shows a graph showing the transition of stresses occurring to the toggle mechanism.

In the graph shown in FIG. 8, the vertical axis represents the stress value (stretching direction is positive, and compressing direction is negative), and the horizontal axis is a time axis, so that it shows the transition of the stress values with the lapse of time from the mold opening state until the mold clamping is completed. The numerals ① through ⑧ plotted in the graph show the measurement spots in the following table.

TABLE 2

| Channel No | Positions for sticking strain gauges |
|---|---|
| ① | Upper tie-bar operation side |
| ② | Upper tie-bar non-operation side |
| ③ | Lower tie-bar operation side |
| ④ | Lower tie-bar non-operation side |
| ⑤ | Upper cross-head link operation side |
| ⑥ | Upper cross-head link non-operation side |
| ⑦ | Lower cross-head link operation side |
| ⑧ | Lower cross-head link non-operation side |

When the toggle mechanism 30 passes the change point as shown in FIG. 7(B) (in FIG. 7(B), it passes the change point by an angle θ), the lower toggle mechanism 30 has to pass the change point again to return to the mold opening state, but the area at the back pressure side of the mold-clamping cylinder 27 is smaller by that of the cylinder rod, and thus sufficient thrust power to make it possible to pass the change point cannot be obtained, thus making it impossible to open the mold only with the mold-clamping cylinder 27. However, by detecting the stress applied to the cross-head link 34 in the lower toggle mechanism 30, the problem related to mold opening can be sensed in advance and correspond to it.

Specifically, in the normal state before the toggle mechanism 30 passes the change point as shown in FIG. 7(A), the stress in a compressing direction is applied to the cross-head link 34. However, when the abrasion in the toggle mechanism 30 develops as shown in FIG. 7(B), and the mid-link 38 and the toggle link 36 pass the change point, the stress in a stretching direction occurs to the cross-head link 34, and stretching stress continues to be applied to the cross-head link 34 hereinafter. Since the strain gauge 40 is stuck to the cross-head link 34 here, the direction in which the stress is applied to the cross-head link 34 and the absolute value of the abrasion amount can be detected. If the relationship between the direction and magnitude of the stress applied to the cross-head link 34 and the abrasion amount of the mid-link 38 is taken into the stress judging means 47 as a stress standard database, it becomes possible to estimate the absolute magnitude of the abrasion amount of the mid-link 38 from the measured stress value of the cross-head link 34, whereby it becomes possible to prevent the toggle mechanism 30 from passing the change point. More specifically, it is suitable if a judgement can be made to make it possible to make inspection and maintenance of the mid-link 38 at the stage in which the value of the stress applied to the cross-head link 34 changes from compression to stretch.

Further, the stress applied to the cross-head link 34 changes in a compressing direction to a stretching direction before or after the toggle mechanism 30 passes the change point, and therefore, if a stress pattern in the cross-head link 34 at the stage in which the stress changes to the stretching direction is stored in the stress judging means 47, the stress pattern and the actual measured value of the stress related to the cross-head link 34 are compared, whereby it becomes possible to judge the state of the mid-link 38.

Though the above-described explanation is about the method for coping with the aged deterioration of the die casting machine 10, the mold-clamping mechanism abnormality monitoring apparatus 44 constituted by the strain gauges 40, the signal amplifier 42, and the stress judging means 47 can detect an unexpected phenomenon occurring to the toggle mechanism 30 by always monitoring the toggle mechanism. For example, when supply shortage of lubricant oil occurs to the pin connecting portion 48 and sliding resistance of the aforementioned pin connecting portion 48 increases, it is detected as a change (increase in many cases) in the stress value of any of the links of the toggle mechanism 30. If the stress value exceeds the stress standard value, it is judged as an abnormality even if it is a new component with less abrasion, and maintenance can be performed.

Figure 10:
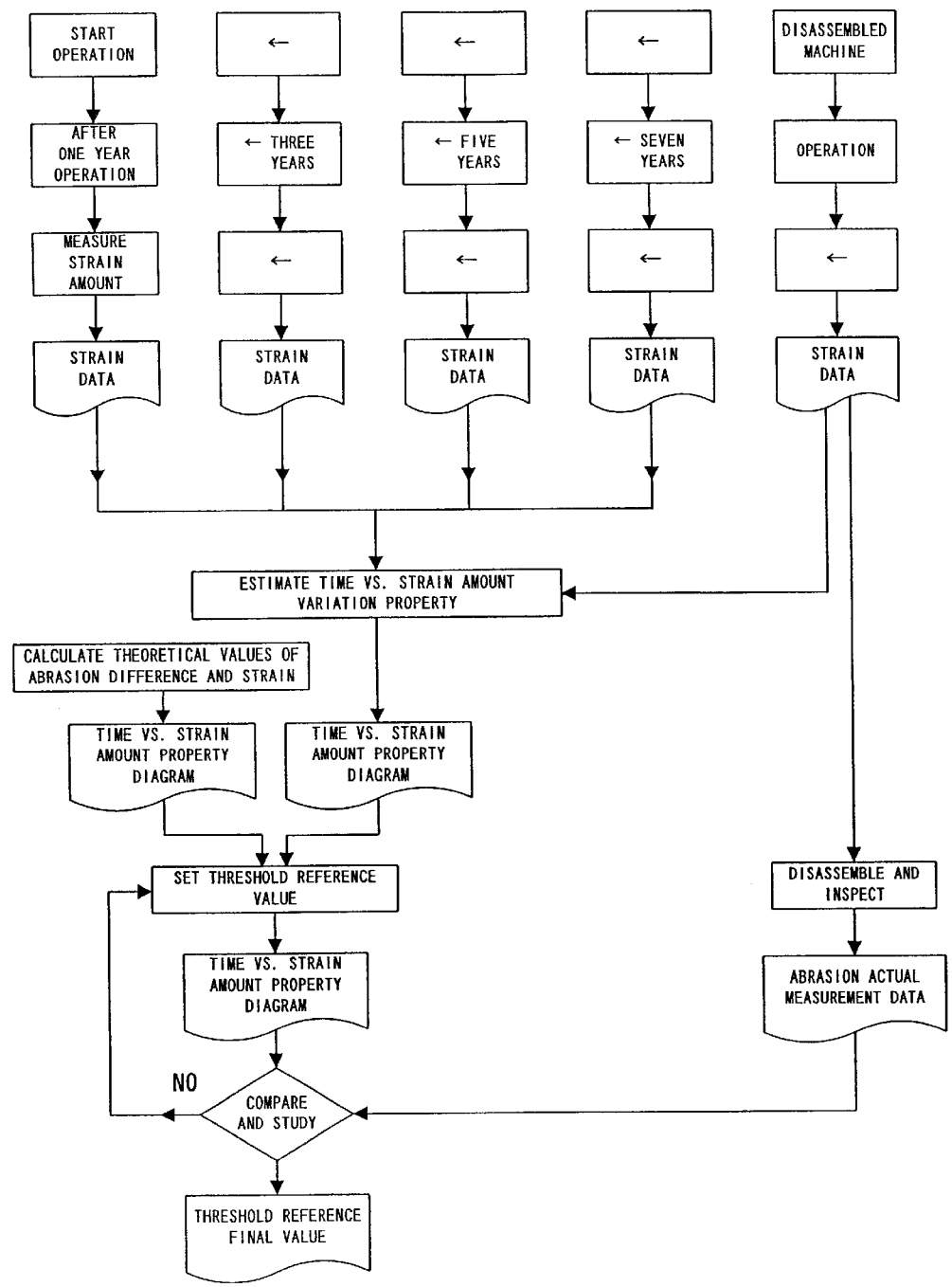
FIG. 10 is an explanatory diagram showing steps of constructing threshold reference data for generating a graph showing an amount of strain (or stress) with respect to the operating years in the mid-link 38 shown in FIG. 9.
Figure 11:
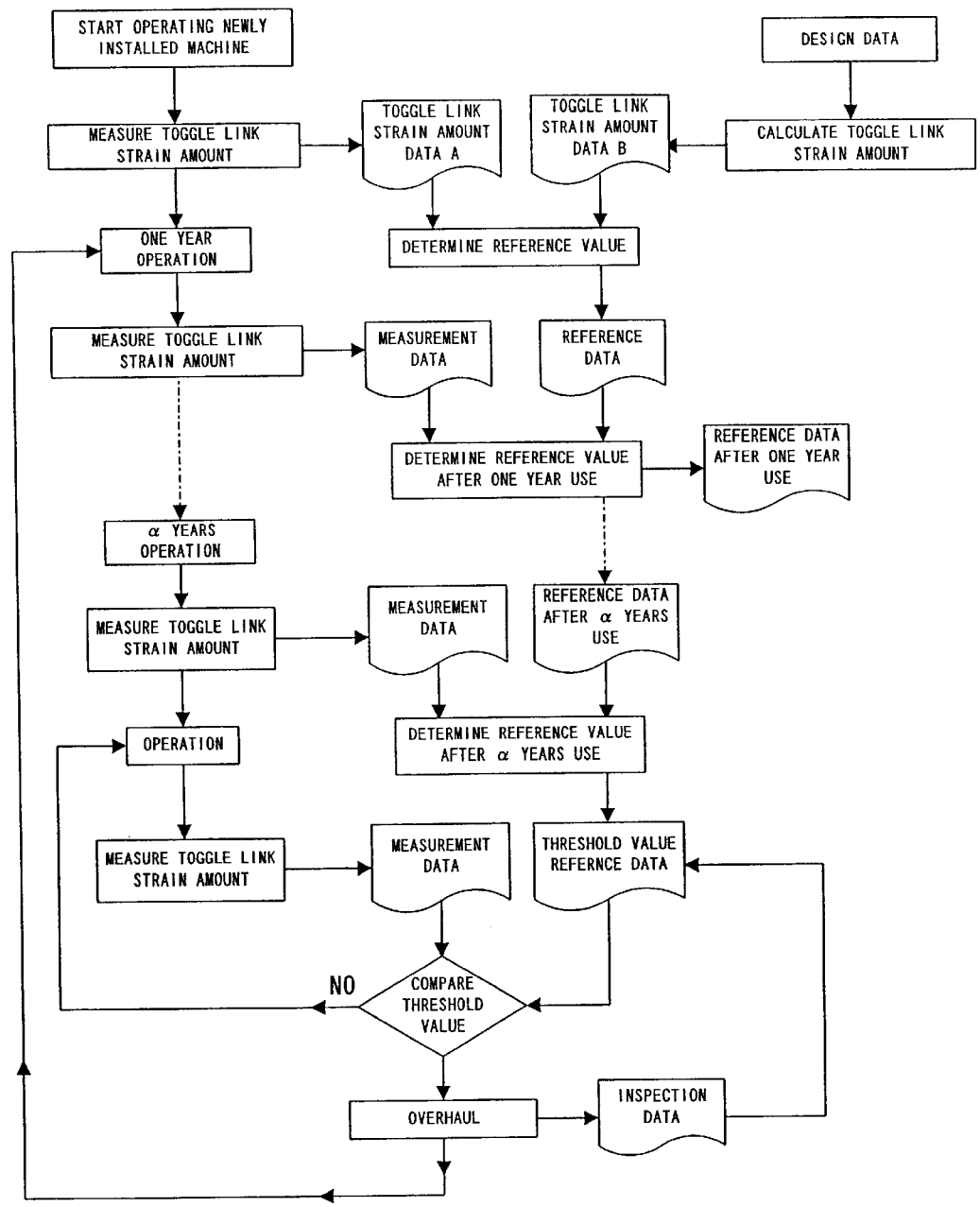
FIG. 11 is an explanatory view showing steps of quality control regarding poor mold-clamping for generating a graph showing an amount of strain (or stress) with respect to the operating years in the mid-link 38 shown in FIG. 9.
Figure 12:
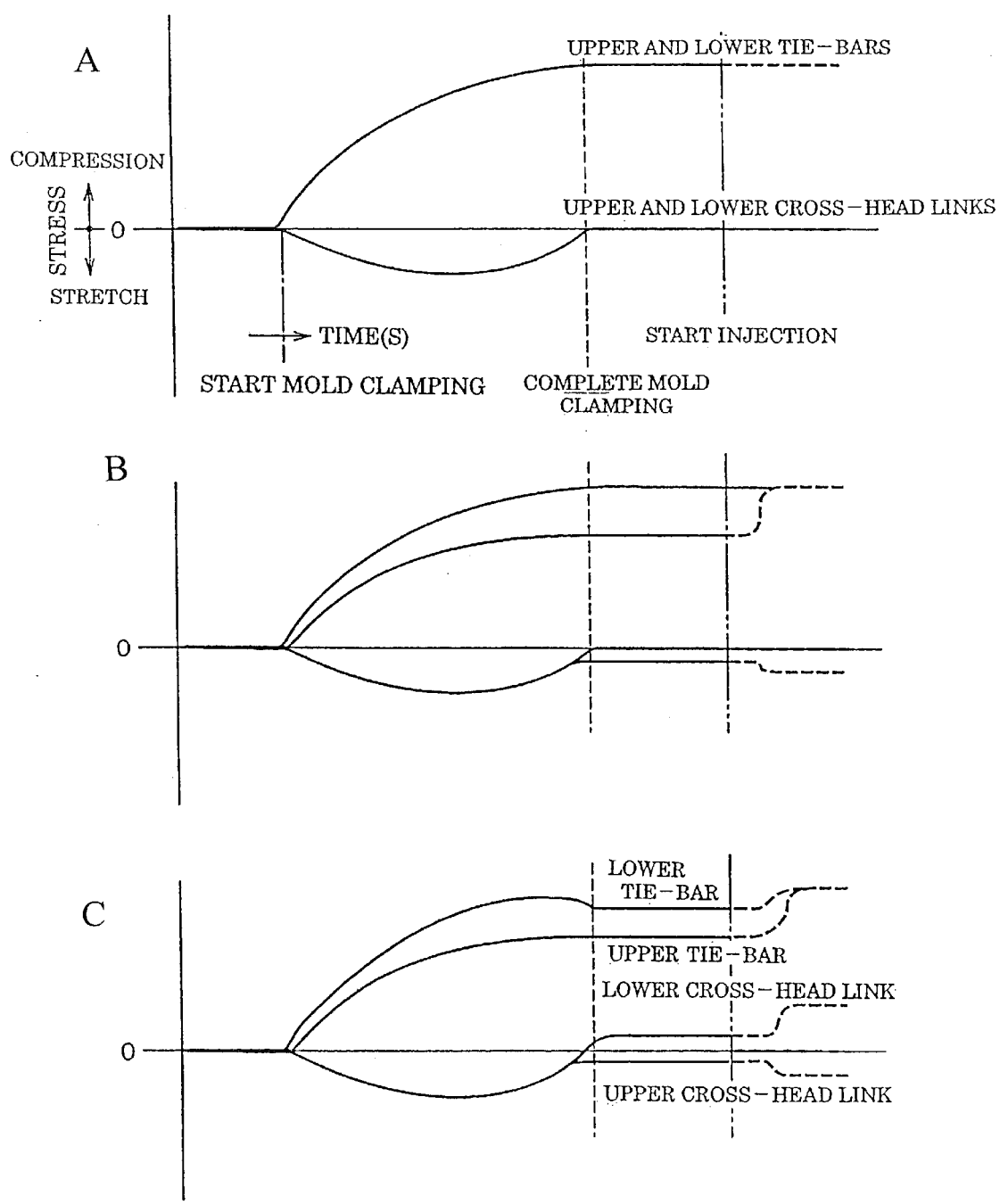
FIG. 12 is a graph showing stress exerted on the crosshead links during mold-clamping.

FIG. 10 is an explanatory view showing procedural steps for constructing threshold reference data for generating the graph showing the amount of strain with respect to the number of operating years in the mid-links 38 shown in FIG. 9. FIG. 11 is an explanatory view showing procedural steps of quality control regarding poor mold-clamping for generating the graph showing the amount of strain with respect to the number of operating years in the mid-links 38 shown in FIG. 9. FIG. 12(A), FIG. 12(B), and FIG. 12(C) are graphs showing the stress exerted on the cross-head links during mold-clamping. Various stresses as shown in FIG. 12 occur to the cross-head links 34 according to the state of the toggle mechanism. More specifically, FIG. 12(A) shows the state in which the stress exerted on the cross-head link 34 is normal, and FIG. 12(B) shows the state in which the rotational shaft bearing portion of the upper cross-head link is abnormally worn, whereby the mold-clamping force of the upper toggle becomes insufficient. Further, FIG. 12(C) shows the state in which the entire toggle mechanism is worn, and a point Bu passes through a line connecting a point Au and a point Cu in the lower toggle, whereby the mold-clamping force is insufficient. If molten metal is injected in this state, the mold-clamping force increases. Meanwhile, the stress of the cross-head link after the passage of the change point becomes a stretching stress, and further increases after molten metal is injected (See the portions shown by the broken lines). If it enters the mold-clamping step in this state, larger force is required since the point Bu passes the change point, and the shortage of the mold-clamping cylinder force occurs, whereby the molding cycle is stopped.

Further as shown in FIG. 11, in order to calculate the abrasion amount from the amount of strain as shown in FIG. 11, it is necessary to measure the strain amount during operation of, for example, the new die casting machine 10, and the strain amounts after the lapse of one year, three, five, and seven years, and actually disassemble the aforementioned die casting machine 10 to obtain the actual measurement value of the abrasion amount (the value of the other same die casting machine may be used). Theoretical values (design values) of the abrasion amount and strain are added to the strain amount and actual abrasion amount, thereby making it possible to set the threshold reference value of strain (See FIG. 9). The properties differ individually even in the same type of the die casting machines 10 due to variations in the components, assembly, and so on. Consequently, the reference value is determined from the theoretical value and the actual measurement value of the strain amount and the reference value after the lapse of predetermined years of operation is determined. The reference value and the actual measurement value after the lapse of operating years may be compared to thereby determine the timing of maintenance.

In the present embodiment, the mid-link 38 and the cross-head link 34 are mainly explained, but this is not restrictive, and various data may be collected based on the value of the other strain gauge 40 stuck to the guide rod 32 to calculate the tendency of the deviation of the mold-clamping force in the die casting machine 10.

According to the invention explained above, the method of monitoring abnormality of the mold-clamping mechanism for the molding machine using the toggle mechanism for the mold-clamping mechanism, includes the steps of measuring the stress exerted on the aforementioned toggle mechanism, and comparing the measured value and the stress standard value set in advance to determined the content and timing of maintenance for the mold-clamping mechanism, and the molding machine using the toggle mechanism for the mold-clamping mechanism provided with the stress measuring means at the aforementioned toggle mechanism, with the stress measuring means being connected to the stress judging means having the stress standard database previously set, measurement value from the aforementioned stress measuring means being taken into the aforementioned stress judging means and checked against the aforementioned stress standard database to output the content and timing of maintenance, thereby estimating the abrasion amount without disassembling and inspecting the mold-clamping mechanism in the molding machine (the time related to the disassembly inspection can be deleted), and making it possible to operate the machine until the time immediately before a quality deficiency of a product occurs, perform maintenance with the minimum disassembly for inspection and improve productivity. Further, since stress variation in the toggle mechanism is always monitored, an abnormal phenomenon can be detected even if an unexpected abnormality occurs to the mold-clamping mechanism.

What is claimed is:

1. A method for monitoring abnormality of a mold-clamping mechanism of a molding machine using a toggle mechanism for a mold-clamping mechanism, comprising the steps of:
   measuring stress exerted on the toggle mechanism; and
   comparing the measured value and a stress standard value set in advance to determine a content and timing of maintenance for the mold-clamping mechanism.

2. A method for monitoring abnormality of a mold-clamping mechanism of a molding machine using, for a mold-clamping mechanism, a plurality of toggle mechanisms having mid-links and cross-head links for extending the mid-links by pressing the mid-links, comprising the steps of:
   measuring stress exerted on a plurality of the mid-links; and
   comparing the measured values and a stress standard value set in advance to estimate abrasion amounts of the mid-links and a difference in the abrasion amounts occurring to the mid-links and determine a content and timing of maintenance.

3. A method for monitoring abnormality of a mold-clamping mechanism of a molding machine using, for a mold-clamping mechanism, a plurality of toggle mechanisms having mid-links and cross-head links for extending the mid-links by pressing the mid-links, comprising the steps of:
   measuring stress occurring to the cross-head links after mold-clamping; and
   comparing the measured values and a stress standard value set in advance to estimate absolute magnitudes of the abrasion amounts of the mid-links and determine a content and timing of maintenance.

4. A method for monitoring abnormality of a mold-clamping mechanism of a molding machine using, for a mold-clamping mechanism, a plurality of toggle mechanisms having mid-links and cross-head links for extending the mid-links by pressing the mid-links, comprising the steps of:
   measuring stress exerted on a plurality of the mid-links and stress occurring to the cross-head links after mold-clamping; and
   comparing the measured values and a stress standard value set in advance to estimate a difference in abrasion amounts occurring to the mid-links and absolute magnitudes of the abrasion amounts of the mid-links and determine a content and timing of maintenance.

5. The method for monitoring abnormality of a mold-clamping mechanism of a molding machine according to claim 2,
   wherein the difference in the abrasion amounts occurring to the mid-links is obtained by using a deviation from a maximum value of the measured values measured at a plurality of the mid-links.

6. The method for monitoring abnormality of a mold clamping mechanism of a molding machine according to claim 2,
   wherein the difference in abrasion amounts occurring to the mid-links is obtained by using a deviation from the measured value of the mid-link to which stress is applied first.

7. The method for monitoring abnormality of a mold-clamping mechanism of a molding machine according to claim 2,
   wherein the toggle mechanism comprises a set of upper and lower cross-head links, and a state of the mid-links at the time of completion of mold-clamping is judged from a stress pattern during one cycle of mold-clamping.

8. The method for monitoring abnormality of a mold-clamping mechanism of a molding machine according to claim 1,
   wherein the stress standard value is larger than a stress value calculated from injection pressure of the molding machine.

9. An apparatus for monitoring abnormality of a mold-clamping mechanism of a molding machine, said molding machine using a toggle mechanism for a mold-clamping mechanism, comprising:
   stress measuring means provided at said toggle mechanism; and
   stress judging means having a stress standard database set in advance, to which said stress measuring means is connected;
   wherein a measured value from said stress measuring means is taken into said stress judging means and checked against said stress standard database and thereby a content and timing of maintenance are outputted.

10. The apparatus for monitoring abnormality of a mold-clamping mechanism of a molding machine according to claim 9, wherein said toggle mechanism comprises a plurality of mid-links and cross-head links for extending the mid-links by pressing the mid-links, and said stress measuring means are provided at the mid-links to make it possible to measure abrasion amounts of said mid-links and difference in the abrasion amounts occurring to the mid-links.

11. The apparatus for monitoring abnormality of a mold-clamping mechanism of a molding machine according to claim 9, wherein said toggle mechanism comprises a plurality of mid-links and cross-head links for extending the mid-links by pressing the mid-links, and said stress measuring means are provided at the cross-head links to make it possible to measure absolute magnitudes of abrasion amounts of said mid-links.

12. The apparatus for monitoring abnormality of a mold-clamping mechanism of a molding machine according to claim 9, wherein said toggle mechanism comprises a plurality of mid-links and cross-head links for extending the mid-links by pressing the mid-links, and said stress measuring means are provided at the mid-links and the cross-head links to make it possible to measure difference in abrasion amounts occurring to said mid-links and absolute magnitudes of the abrasion amounts of said mid-links.

13. The apparatus for monitoring abnormality of a mold-clamping mechanism of a molding machine according to claim 9, wherein a strain gauge is used for said stress measuring means, and stress is calculated based on a value of the strain gauge.

14. The method for monitoring abnormality of a mold-clamping mechanism of a molding machine according to claim 4, wherein the difference in the abrasion amounts occurring to the mid-links is obtained by using a deviation from a maximum value of the measured values measured at a plurality of the mid-links.

15. The method for monitoring abnormality of a mold clamping mechanism of a molding machine according to claim 4, wherein the difference in abrasion amounts occurring to the mid-links is obtained by using a deviation from the measured value of the mid-link to which stress is applied first.

16. The method for monitoring abnormality of a mold-clamping mechanism of a molding machine according to claim 3, wherein the toggle mechanism comprises a set of upper and lower cross-head links, and a state of the mid-links at the time of completion of mold-clamping is judged from a stress pattern during one cycle of mold-clamping.

17. The method for monitoring abnormality of a mold-clamping mechanism of a molding machine according to claim 4, wherein the toggle mechanism comprises a set of upper and lower cross-head links, and a state of the mid-links at the time of completion of mold-clamping is judged from a stress pattern during one cycle of mold-clamping.

18. The method for monitoring abnormality of a mold-clamping mechanism of a molding machine according to claim 2, wherein the stress standard value is larger than a stress value calculated from injection pressure of the molding machine.

19. The method for monitoring abnormality of a mold-clamping mechanism of a molding machine according to claim 3, wherein the stress standard value is larger than a stress value calculated from injection pressure of the molding machine.

20. The method for monitoring abnormality of a mold-clamping mechanism of a molding machine according to claim 4, wherein the stress standard value is larger than a stress value calculated from injection pressure of the molding machine.

21. The apparatus for monitoring abnormality of a mold-clamping mechanism of a molding machine according to claim 10, wherein a strain gauge is used for said stress measuring means, and stress is calculated based on a value of the strain gauge.

22. The apparatus for monitoring abnormality of a mold-clamping mechanism of a molding machine according to claim 11, wherein a strain gauge is used for said stress measuring means, and stress is calculated based on a value of the strain gauge.

23. The apparatus for monitoring abnormality of a mold-clamping mechanism of a molding machine according to claim 12, wherein a strain gauge is used for said stress measuring means, and stress is calculated based on a value of the strain gauge.

* * * * *